*(12)* United States Patent
Toba

(10) Patent No.: US 10,111,625 B2
(45) Date of Patent: Oct. 30, 2018

(54) BIOPSY APPARATUS AND OPERATION METHOD THEREOF

(71) Applicant: FUJIFILM Corporation, Tokyo (JP)

(72) Inventor: Hiroyuki Toba, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 468 days.

(21) Appl. No.: 14/972,316

(22) Filed: Dec. 17, 2015

(65) Prior Publication Data

US 2016/0183887 A1 Jun. 30, 2016

(30) Foreign Application Priority Data

Dec. 24, 2014 (JP) .................................. 2014-261272

(51) Int. Cl.
| | | |
|---|---|---|
| *A61B 6/00* | (2006.01) | |
| *A61B 6/02* | (2006.01) | |
| *A61B 10/02* | (2006.01) | |
| *A61B 6/04* | (2006.01) | |
| *A61B 6/12* | (2006.01) | |
| *A61B 34/20* | (2016.01) | |
| *A61B 10/04* | (2006.01) | |

(52) U.S. Cl.
CPC .............. *A61B 6/025* (2013.01); *A61B 6/022* (2013.01); *A61B 6/0414* (2013.01); *A61B 6/12* (2013.01); *A61B 6/461* (2013.01); *A61B 6/502* (2013.01); *A61B 6/5223* (2013.01); *A61B 6/582* (2013.01); *A61B 10/0233* (2013.01); *A61B 34/20* (2016.02); *A61B 2010/0208* (2013.01); *A61B 2010/045* (2013.01)

(58) Field of Classification Search
CPC ........... A61B 6/025; A61B 6/022; A61B 6/12; A61B 6/502; A61B 34/20
See application file for complete search history.

(56) References Cited

U.S. PATENT DOCUMENTS

| | | |
|---|---|---|
| 5,964,715 A | 10/1999 | Thunberg |
| 2006/0098855 A1 | 5/2006 | Gkanatsios et al. |
| 2011/0222758 A1 | 9/2011 | Kanagawa et al. |
| 2014/0073913 A1 | 3/2014 | Defreitas et al. |

FOREIGN PATENT DOCUMENTS

| | | |
|---|---|---|
| JP | 10-201749 A | 8/1998 |
| JP | 2013-13651 A | 8/1998 |
| JP | 2009-526618 A | 7/2009 |
| JP | 2010-75316 A | 4/2010 |
| JP | 2012-245329 A | 12/2012 |

OTHER PUBLICATIONS

Extended European Search Report, dated Jun. 2, 2016, for European Application No. 15197383.1.

*Primary Examiner* — Joseph M Santos Rodriguez
(74) *Attorney, Agent, or Firm* — Birch, Stewart, Kolasch & Birch, LLP

(57) ABSTRACT

A position of a target designated based on a tomosynthesis image is identified as a first designated position. The first designated position is virtually projected to a radiation detector from two calibrated-stereotactic tube positions which have been calibrated into a tomosynthesis coordinate system so as to obtain two projection positions. The first designated position is converted into a second designated position in a stereotactic coordinate system based on stereotactic tube positions and the projection positions. A biopsy needle is inserted into a subject to be examined based on the second designated position. The biopsy needle is driven based on a biopsy coordinate system calibrated with respect to the stereotactic coordinate system.

6 Claims, 13 Drawing Sheets

BIOPSY APPARATUS AND OPERATION METHOD THEREOF

CROSS-REFERENCE TO RELATED APPLICATIONS

The present application claims priority under 35 U.S.C. § 119 to Japanese Patent Application No. 2014-261272, filed Dec. 24, 2014. The above application is hereby expressly incorporated by reference, in its entirety, into the present application.

BACKGROUND OF THE INVENTION

1. Field of the Invention

The present invention relates to a biopsy apparatus for identifying a lesion position based on a tomosynthesis image and extracting a piece of tissue from the lesion position, and an operation method of the biopsy apparatus.

2. Description Related to the Prior Art

A biopsy apparatus intended for extracting a piece of tissue from a lesion (tumor or calcification) of a patient and conducting a detailed examination for medical diagnosis has been developed. The biopsy apparatus inserts a hollow biopsy needle into a subject to be examined (breast or the like) of a patient, so as to extract a piece of tissue which enters into the biopsy needle.

As the biopsy apparatus, there is a stereotactic biopsy apparatus, in which stereotactic imaging is performed on a subject to be examined by using radiation, so as to obtain two radiographic images (i.e., stereotactic image) and identify a three-dimensional position of the lesion with use of the obtained two radiographic images, and then a biopsy needle is moved based on the identified position.

Specifically, in the stereotactic biopsy apparatus, a tube of a radiation source is moved to two positions each having a different angle relative to the subject to be examined (i.e., stereotactic tube positions), and radiation is irradiated from the tube at each of the stereotactic tube positions. Then, an image of the radiation having passed through the subject to be examined is captured by a radiation detector, and thus each of the radiographic images constituting the stereotactic image is generated. The stereotactic image is displayed on a monitor. A user such as a doctor designates a lesion position as a target, into which the biopsy needle is to be inserted, in each of the radiographic images. Three-dimensional position information of the designated lesion position is calculated based on the stereotactic image, and the biopsy needle is moved in accordance with the calculated lesion position.

The stereotactic biopsy apparatus recognizes each of the lesion position and the position at which the biopsy needle is to be inserted as a position in a three-dimensional coordinate system, and controls movement of the biopsy needle. Accordingly, a biopsy coordinate system for use in the control of the movement of the biopsy needle and a stereotactic coordinate system for use in the stereotactic imaging for recognizing the lesion position should be coincident with each other exactly. In order to ensure that the biopsy coordinate system and the stereotactic coordinate system are coincident with each other, in principal, it is sufficient to design a movement mechanism of the tube and the biopsy needle and the like with a high degree of accuracy and perform positioning by mechanical adjustment, so as to avoid deviation between the biopsy coordinate system and the stereotactic coordinate system.

However, since the degree of deviation practically acceptable is as small as at most about 1 mm, it is difficult to achieve the acceptable degree of accuracy by the mechanical adjustment of the movement mechanism of the tube and the biopsy needle and the like. Therefore, calibration between the biopsy coordinate system and the stereotactic coordinate system is performed before using the biopsy apparatus, so as to acquire calibration data for associating the biopsy coordinate system with the stereotactic coordinate system (see Japanese Patent Laid-Open Publication No. 2010-75316). In order to control the movement of the biopsy needle, the lesion position identified in the stereotactic coordinate system is converted into a corresponding position in the biopsy coordinate system, and the movement of the biopsy needle is controlled based on the corresponding position obtained by the conversion.

Further, recently, tomosynthesis imaging has been known. In the tomosynthesis imaging, the tube of the radiation source is moved to capture an image of the subject to be examined of a patient from a plurality of directions, and a plurality of tomographic images are reconstructed from a plurality of radiographic images obtained by the image capturing (i.e., projection images) by image processing. The plurality of tomographic images are referred to as a tomosynthesis image, and have three-dimensional information of the subject to be examined. The tomosynthesis image is a high-definition three-dimensional image making it easier to confirm the lesion at which tissues are overlapped with each other, and used as a clinical diagnostic image.

A tomosynthesis biopsy apparatus obtained by adding the tomosynthesis imaging function to the biopsy apparatus, which is capable of designating the lesion position (target) based on the tomosynthesis image, has been known (see United States Patent Application Publication No. 2014/0073913 corresponding to Published Japanese translation of PCT application No. 2009-526618). It is necessary to designate the lesion position in each of the radiographic images constituting the stereotactic image in the stereotactic biopsy apparatus. In contrast, the tomosynthesis biopsy apparatus has an advantage in that three-dimensional position information of the lesion position can be acquired by finding the tomographic image in which the lesion appears from the tomosynthesis image and designating the lesion position in the tomographic image only once. Further, there is a lesion which is not visible in the stereotactic image but which is visible in the tomosynthesis image, and therefore the tomosynthesis biopsy apparatus also has an advantage in that such a lesion can be subjected to the biopsy.

Additionally, a biopsy apparatus obtained by adding the tomosynthesis imaging function to the stereotactic biopsy apparatus, which is capable of performing both the tomosynthesis imaging and the stereotactic imaging, has been known (see Japanese Patent Laid-Open Publication No. 2012-245329).

As disclosed in Japanese Patent Laid-Open Publication No. 2010-75316, calibration between the stereotactic coordinate system and the biopsy coordinate system is normally performed in the stereotactic biopsy apparatus, and calibration data for associating the stereotactic coordinate system with the biopsy coordinate system is acquired.

In the case where the tomosynthesis imaging function is added to the stereotactic biopsy apparatus and the target is designated based on the tomosynthesis image as disclosed in Japanese Patent Laid-Open Publication No. 2012-245329, it is necessary to associate the tomosynthesis coordinate system with the biopsy coordinate system.

In the tomosynthesis imaging, the tube of the radiation source is set to a lot of positions for the purpose of the image capturing. An error in setting each of the positions of the tube results in deviation of the tomosynthesis coordinate system. Therefore, it is perceived that the amount of deviation of the tomosynthesis coordinate system from the biopsy coordinate system is larger than the amount of deviation of the stereotactic coordinate system from the biopsy coordinate system.

Accordingly, in the case where the target is designated based on the tomosynthesis image, it is necessary to perform calibration between the coordinate systems with a higher degree of accuracy in comparison with the case where the target is designated based on the stereotactic image.

However, in order to perform calibration for associating the tomosynthesis coordinate system with the biopsy coordinate system, it is necessary to create calibration data by a procedure in which a calibration biopsy needle, for example, is driven to perform the tomosynthesis imaging, and position information of a tip portion of the calibration biopsy needle in the biopsy coordinate system is compared with position information of a tip portion of the calibration biopsy needle obtained by the tomosynthesis imaging, as disclosed in Japanese Patent Laid-Open Publication No. 2010-75316. As described above, the calibration between the tomosynthesis coordinate system and the biopsy coordinate system with a high degree of accuracy is troublesome and a burden to a user. Further, in the case where the calibration between the tomosynthesis coordinate system and the biopsy coordinate system is not performed, although the lesion position in the subject to be examined can be identified with a high degree of accuracy by the tomosynthesis imaging, deviation between the lesion position and the position into which the biopsy needle is inserted may occur.

SUMMARY OF THE INVENTION

An object of the present invention is to provide a biopsy apparatus capable of readily associating a tomosynthesis coordinate system with a biopsy coordinate system and inserting a biopsy needle with a high degree of accuracy based on a position of a target designated based on the tomosynthesis image, and an operation method of the biopsy apparatus.

To achieve the above and other objects of the present invention, a biopsy apparatus of the present invention includes a radiation source, a radiation detector, a stereotactic image generator, a tomosynthesis image generator, a biopsy needle driver, a designated-target position identification section, and a target position conversion section. The radiation source irradiates radiation toward a subject to be examined from a tube. The radiation detector detects radiation which has been irradiated from the radiation source and passed through the subject so as to generate a radiographic image. The stereotactic image generator generates a stereotactic image, which consists of two radiographic images generated by the radiation detector and is represented by a stereotactic coordinate system, by irradiating radiation from the tube disposed at two stereotactic tube positions each having a different angle relative to the subject. The tomosynthesis image generator generates a tomosynthesis image, which is represented by a tomosynthesis coordinate system, by irradiating radiation from the tube disposed at a plurality of tomosynthesis tube positions each having a different angle relative to the subject and performing reconstruction of a plurality of tomographic images from a plurality of radiographic images generated by the radiation detector. The biopsy needle driver drives a biopsy needle based on a biopsy coordinate system calibrated with respect to the stereotactic coordinate system so as to insert the biopsy needle into the subject. The designated-target position identification section identifies a position of a target designated based on the tomosynthesis image as a first designated position. The target position conversion section obtains two projection positions by virtually projecting the first designated position to the image detector from two calibrated-stereotactic tube positions which have been calibrated into the tomosynthesis coordinate system, and converts the first designated position into a second designated position in the stereotactic coordinate system based on the stereotactic tube positions and the projection positions.

The biopsy apparatus further includes a tube position information correction section for correcting the stereotactic tube positions and the tomosynthesis tube positions based on setting error information of the tube. Preferably, the tomosynthesis image generator performs the reconstruction based on the tomosynthesis tube positions corrected by the tube position information correction section, and the target position conversion section obtains the second designated position based on the stereotactic tube positions corrected by the tube position information correction section.

The target position conversion section preferably obtains an intersection between a first virtual straight line and a second virtual straight line as the second designated position. The first virtual straight line connects a first projection position and a first stereotactic tube position, and the second virtual straight line connects a second projection position and a second stereotactic tube position. The first projection position is obtained by virtually projecting the first designated position from a first calibrated-stereotactic tube position of the two calibrated-stereotactic tube positions toward the image detector. The first stereotactic tube position of the two stereotactic tube positions corresponds to the first calibrated-stereotactic tube position. The second projection position is obtained by virtually projecting the first designated position from a second calibrated-stereotactic tube position of the two calibrated-stereotactic tube positions toward the image detector. The second stereotactic tube position of the two stereotactic tube positions corresponds to the second calibrated-stereotactic tube position.

Preferably, the biopsy apparatus further includes a display part on which the tomosynthesis image is displayed, and an operation part for allowing a user to designate a position of the target based on the tomosynthesis image displayed on the display part. The designated-target position identification section preferably identifies a position in the tomosynthesis coordinate system, which is designated by the operation part, as the first designated position.

Preferably, the biopsy apparatus further includes a calibration controller for making the tomosynthesis image generator generate a tomosynthesis image in a state that an object to be imaged is a phantom having a pseudo target so as to detect a position of the pseudo target in the tomosynthesis coordinate system, and making the stereotactic image generator generate a stereotactic image so as to detect a position on the radiation detector toward which the pseudo target is projected, and identifying a position of the tube in a direction connecting the position toward which the pseudo target is projected and the position of the pseudo target in the tomosynthesis coordinate system as the calibrated-stereotactic tube position.

Preferably, the biopsy apparatus further includes a memory part in which calibration data for associating the biopsy coordinate system with the stereotactic coordinate system is stored. The biopsy needle driver preferably corrects a deviation amount between the biopsy coordinate system and the stereotactic coordinate system based on the calibration data, and then drives the biopsy needle.

According to an operation method of a biopsy apparatus of the present invention, the biopsy apparatus includes: a radiation source for irradiating radiation toward a subject to be examined from a tube; a radiation detector for detecting radiation which has been irradiated from the radiation source and passed through the subject so as to generate a radiographic image; a stereotactic image generator for generating a stereotactic image, which consists of two radiographic images generated by the radiation detector and is represented by a stereotactic coordinate system, by irradiating radiation from the tube disposed at two stereotactic tube positions each having a different angle relative to the subject; a tomosynthesis image generator for generating a tomosynthesis image, which is represented by a tomosynthesis coordinate system, by irradiating radiation from the tube disposed at a plurality of tomosynthesis tube positions each having a different angle relative to the subject and performing reconstruction of a plurality of tomographic images from a plurality of radiographic images generated by the radiation detector; and a biopsy needle driver for driving a biopsy needle based on a biopsy coordinate system calibrated with respect to the stereotactic coordinate system so as to insert the biopsy needle into the subject. The operation method includes a target position identifying step, a target position converting step, and an inserting step. In the target position identifying step, a position of a target designated based on the tomosynthesis image is identified as a first designated position. In the target position converting step, two projection positions are obtained by virtually projecting the first designated position to the image detector from two calibrated-stereotactic tube positions which have been calibrated into the tomosynthesis coordinate system, and converting the first designated position into a second designated position in the stereotactic coordinate system based on the stereotactic tube positions and the projection positions. In the inserting step, the biopsy needle is inserted into the subject based on the second designated position.

According to the present invention, the position of the target designated based on the tomosynthesis image is determined as the first designated position, the first designated position is virtually projected toward the radiation detector from two calibrated-stereotactic tube positions which have been calibrated into the tomosynthesis coordinate system so as to obtain the two projection positions, and the first designated position is converted into the second designated position in the stereotactic coordinate system based on the stereotactic tube positions and the projection positions. Therefore, it is possible to readily associate the tomosynthesis coordinate system with the biopsy coordinate system, such that the position of the target designated based on the tomosynthesis image is coincident with the position to be inserted by the biopsy needle with a high degree of accuracy.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein.

DESCRIPTION OF THE PREFERRED EMBODIMENTS

First Embodiment

Figure 1:
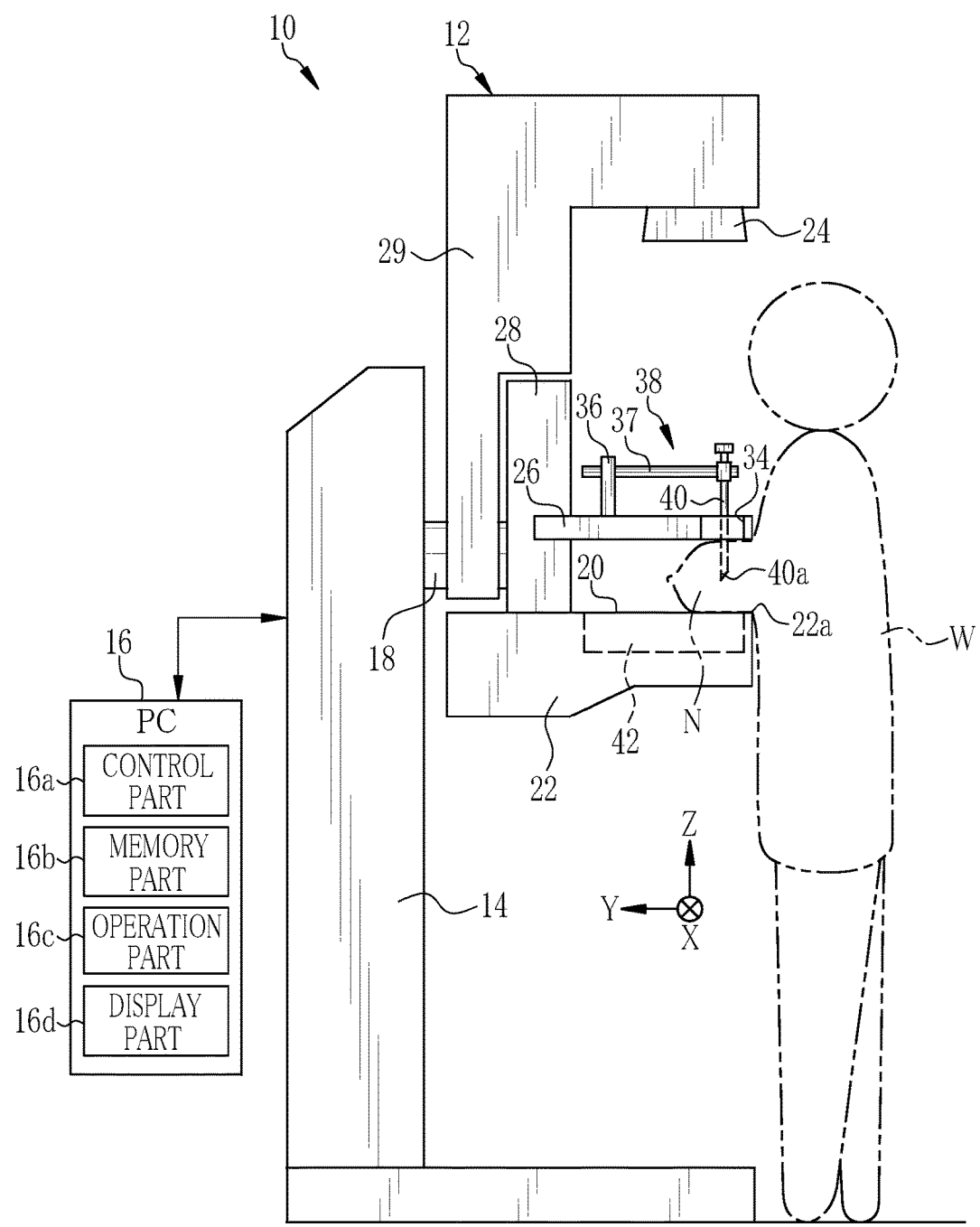
FIG. 1 is a schematic side elevational view of a biopsy apparatus.

As shown in FIG. 1, a biopsy apparatus 10 includes an imaging unit 12, a base 14, and a personal computer (PC) 16. The imaging unit 12 captures an image of a breast N of a subject W in an upright posture using radiation (e.g., X-rays). The base 14 supports the imaging unit 12 from a rear side of the biopsy apparatus 10. The biopsy apparatus 10 consists of a mammography apparatus for capturing an image of a breast N as a subject to be examined, to which a biopsy function is added, for example.

The PC 16 includes a control part 16a consisting of a CPU (Central Processing Unit) and the like, a memory part 16b consisting of a RAM (Random Access Memory), a ROM (Read Only Memory) and the like, an operation part 16c consisting of a keyboard, a mouse, and the like, and a display part 16d consisting of LCD (Liquid Crystal Display) and the like. The PC 16 controls an overall operation of the biopsy apparatus 10, generates an image, displays an image, and receives instructions for operation from a user.

The imaging unit 12 includes an imaging table 22, a pressing plate 26, and a holder section 28. The imaging table 22 has a planar imaging surface 20 coming in contact with the breast N of the subject W. The pressing plate 26 compresses the breast N against the imaging surface 20 of the imaging table 22. The holder section 28 holds the imaging table 22 and the pressing plate 26.

A biopsy hand section 38 for extracting a piece of tissue from the breast N is attached to the pressing plate 26. A rectangular opening 34 is formed on the pressing plate 26 so as to extract the tissue using the biopsy hand section 38. The biopsy hand section 38 consists of a post section 36 disposed on the pressing plate 26 and an arm section 37 having one end connected to the post section 36. A biopsy needle 40 is mounted on the other end of the arm section 37. The biopsy needle 40 is hollow. A piece of tissue is sucked to be extracted through a tip portion 40a of the biopsy needle 40 from the breast N. Incidentally, the biopsy hand section 38 and a biopsy needle driving section 54 to be described later may be unitized as a biopsy unit, and such a biopsy unit may be detachably attached to the holder section 38, the pressing plate 26, or the like.

The biopsy needle 40 can be moved by the biopsy hand section 38 in a direction parallel to a surface of the pressing plate 26 (i.e., direction of X and Y axes, hereinafter referred to as X-Y direction) and in a direction perpendicular to the surface of the pressing plate 26 (i.e., direction of a Z axis, hereinafter referred to as Z direction). Further, the biopsy needle 40 can be tilted at an arbitrary angle with respect to the Z axis by the biopsy hand section 38. In this embodiment, the biopsy needle 40 is moved in the Z direction from the pressing plate 26 to the imaging surface 20 such that the biopsy needle 40 passes through the opening 34 of the pressing plate 26. Thereby, the tip portion 40a of the biopsy needle 40 is inserted into the breast N. Namely, the biopsy needle 40 is driven in a three-dimensional coordinate system. Hereinbelow, the three-dimensional coordinate system for the biopsy, in which the biopsy needle 40 is driven, is referred to as a biopsy coordinate system. The X-coordinate in the biopsy coordinate system is denoted by $X_1$, the Y-coordinate in the biopsy coordinate system is denoted by $Y_1$, and the Z-coordinate in the biopsy coordinate system is denoted by $Z_1$.

Additionally, the imaging unit 12 includes a radiation source 24 having a tube 24a (see FIG. 3) for irradiating radiation, and a support section 29 for supporting the radiation source 24. The tube 24a irradiates cone-beam radiation toward the imaging surface 20. A rotation shaft 18 is provided to the base 14 in a rotatable manner. The rotation shaft 18 is fixed to the support section 29 such that the rotation shaft 18 and the support section 29 rotate together.

The rotation shaft 18 is connected to the holder section 28. The holder section 28 is configured to be switchable between a first state and a second state. In the first state, the rotation shaft 18 is rotated independently from the holder section 28 (i.e., in an idle rotation state). In the second state, the rotation shaft 18 is coupled to the holder section 28 and rotated together with the holder section 28. More specifically, gears (not shown in the drawing) are provided to the rotation shaft 18 and the holder section 28, and the gears can be switched between a non-meshed state (i.e., the first state) and a meshed state (i.e., the second state).

The holder section 28 supports the imaging table 22 such that the imaging surface 20 and the radiation source 24 are separated from each other at a predetermined distance. Further, the holder section 28 holds the pressing plate 26 such that the pressing plate 26 can be slid in the Z direction. The holder section 28 changes a distance between the pressing plate 26 and the imaging surface 20 by sliding the pressing plate 26 in the Z direction.

The imaging surface 20 is made of a material having high radiotransparency and high strength (e.g., carbon). A radiation detector 42 for generating a radiographic image is disposed inside the imaging table 22. The radiation detector 42 detects radiation which has been irradiated from the radiation source 24 and passed through the pressing plate 26, the breast N, and the imaging surface 20, and outputs the radiographic image of the breast N as a digital radiographic image.

Figure 2:
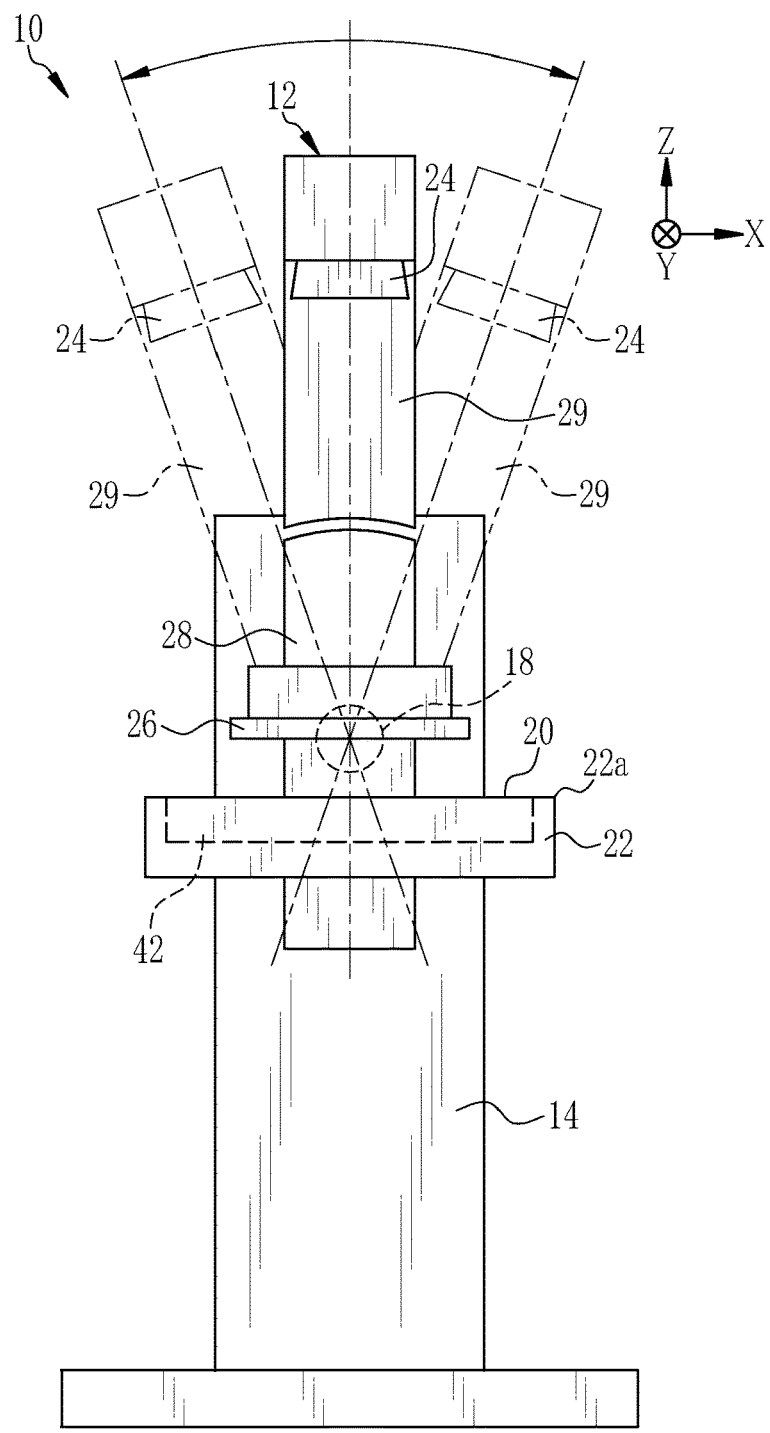
FIG. 2 is a schematic front elevational view of the biopsy apparatus.

In the first state, the rotation shaft 18 is engaged with the holder section 28. As shown in FIG. 2, the biopsy apparatus 10 can move the radiation source 24 in an arc-like manner with respect to the imaging table 22 by rotating the support section 29 in a state that the holder section 28 remains to be fixed. Accordingly, in the first state, it is possible to change the orientation of the radiation source 24 with respect to the imaging surface 20 of the imaging surface 20, for the purpose of capturing an image.

Figure 3:
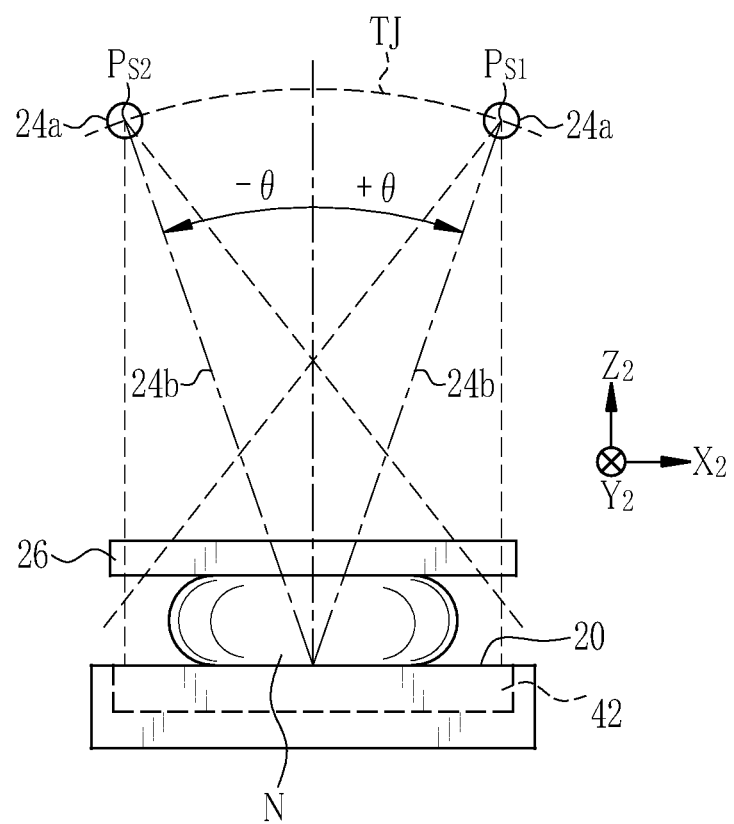
FIG. 3 is a view illustrating stereotactic tube positions.

The biopsy apparatus 10 enables stereotactic imaging, in which the position of the tube 24a of the radiation source 24 is set to a pair of tube positions $P_{S1}$ and $P_{S2}$ and image capturing is performed at each of the tube positions $P_{S1}$ and $P_{S2}$, so as to generate two radiographic images (i.e., stereotactic image), as shown in FIG. 3. The tube position $P_{S1}$ is referred to as a stereotactic tube position $P_{S1}$, and the tube position $P_{S2}$ is referred to as a stereotactic tube position $P_{S2}$. Further, the stereotactic tube position $P_{S1}$ is referred to as a first stereotactic tube position $P_{S1}$, and the stereotactic tube position $P_{S2}$ is referred to as a second stereotactic tube position $P_{S2}$.

The first stereotactic tube position $P_{S1}$ is a position at which the radiation source 24 is tilted at an angle of +θ° in the X direction from a state that an optical axis 24b of the tube 24a is perpendicular to the imaging surface 20. The second stereotactic tube position $P_{S2}$ is a position at which the radiation source 24 is tilted at an angle of −θ° in the X direction from a state that the optical axis 24b of the tube 24a is perpendicular to the imaging surface 20. The angle θ is 15°, for example.

Operation in accordance with a triangulation method is carried out based on the stereotactic image, so as to identify a three-dimensional position of the lesion (tumor or calcification) occurring in the breast N. The first stereotactic tube position $P_{S1}$ and the second stereotactic tube position $P_{S2}$ are related to identification of the lesion position in the breast N. Therefore, deviation of the set positions of the first stereotactic tube position $P_{S1}$ and the second stereotactic tube position $P_{S2}$ results in deviation of the coordinates of the lesion position to be identified. The deviation is equivalent to deviation of the coordinate system for use in the stereotactic imaging (hereinafter referred to as stereotactic coordinate system) relative to the biopsy coordinate system for use in the biopsy. Hereinafter, an X-coordinate in the stereotactic coordinate system is denoted by $X_2$, a Y-coordinate in the stereotactic coordinate system is denoted by $Y_2$, and a Z-coordinate in the stereotactic coordinate system is denoted by $Z_2$.

Figure 4:
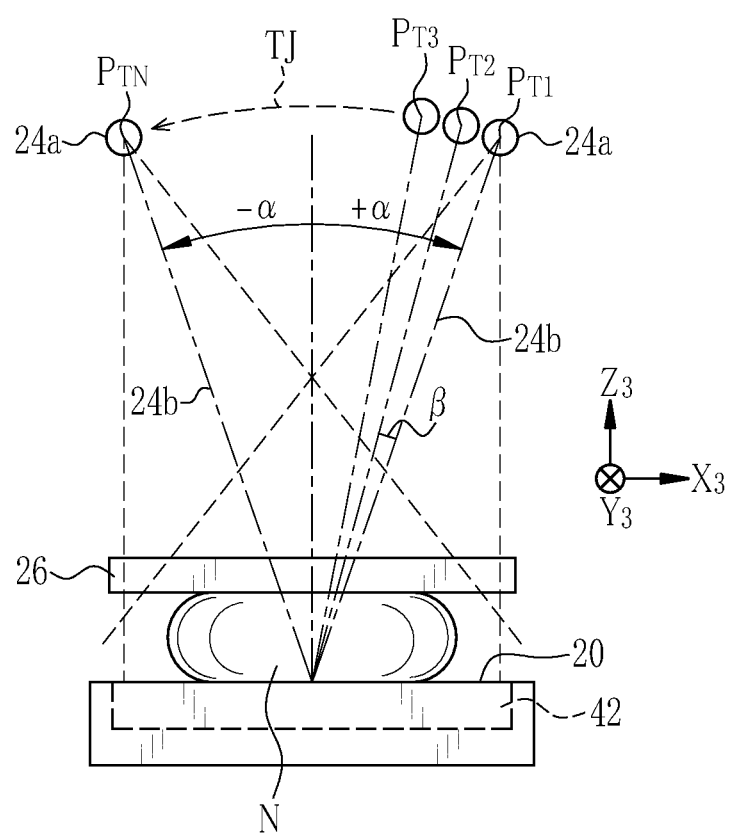
FIG. 4 is a view illustrating tomosynthesis tube positions.

Further, the biopsy apparatus 10 enables tomosynthesis imaging, in which the position of the tube 24a of the radiation source 24 is set to N number of tube positions $P_{T1}$ to $P_{TN}$, and image capturing is performed at each of the tube positions $P_{T1}$ to $P_{TN}$ so as to generate N number of radiographic images (i.e., projection images) and reconstruct a plurality of tomographic images, as shown in FIG. 4. The plurality of tomographic images are referred to as tomosynthesis image. The tube positions $P_{T1}$ to $P_{TN}$ are referred to as tomosynthesis tube positions $P_{PT}$ to $P_{TN}$.

The tomosynthesis tube position $P_{T1}$ is a position at which the radiation source 24 is tilted at an angle of α° in the X direction from a state that an optical axis 24b of the tube 24a is perpendicular to the imaging surface 20. The tomosynthesis tube position $P_{TN}$ is a position at which the radiation source 24 is tilted at an angle of −α° in the X direction from a state that the optical axis 24b of the tube 24a is perpendicular to the imaging surface 20. The angle α is, for example, the same as the angle θ, namely, 15°. The tube 24a is moved by an angle of β each time from the position $P_{T1}$ at which the radiation source 24 is tilted at an angle of +α°, such that the tube 24a is set to the tomosynthesis tube positions $P_{T2}$ to $P_{TN}$ in this order. The angle β is a value satisfying the relation represented by "β=2α/N". N is set to "15", for example.

A user such as a doctor uses the tomosynthesis image to designate the lesion position in this embodiment. The tomosynthesis tube positions $P_{T1}$ to $P_{TN}$ are related to reconstruction of the tomosynthesis image. Therefore, deviation of the set positions of tomosynthesis tube positions $P_{T1}$ to $P_{TN}$ results in deviation of the coordinates of the designated lesion position. The deviation is equivalent to deviation occurring in the coordinate system for use in the tomosynthesis imaging (hereinafter referred to as tomosynthesis coordinate system) relative to the biopsy coordinate system for use in the biopsy. Hereinafter, an X-coordinate in the tomosynthesis coordinate system is denoted by $X_3$, and a Y-coordinate in the tomosynthesis coordinate system is denoted by $Y_3$, and a Z-coordinate in the tomosynthesis coordinate system is denoted by $Z_3$.

In the second state, the rotation shaft 18 is engaged with the holder section 28. The biopsy apparatus 10 can move the radiation source 24 together with the imaging table 22 by rotating the support section 29. Accordingly, in the second state, it is possible to perform both Cranio and Caudal (CC) imaging and Mediolateral-Oblique (MLO) imaging on the breast N.

During the CC imaging, the orientation of the holder section 28 is adjusted to a state that the imaging surface 20 faces upward. Further, the orientation of the holder section 28 is adjusted to a state that the radiation source 24 is positioned above the imaging surface 20. Radiation is thereby irradiated from the radiation source 24 to the breast N from the head side to the feet side of the subject W in the upright posture so as to perform the CC imaging.

During the MLO imaging, the orientation of the holder section 28 is adjusted, such that the imaging table 22 is rotated by an angle of 45° up to 90°, for example, in comparison with the imaging table 22 during the CC imaging. Then, positioning is performed to make the axilla of the subject W contact with a side-wall corner portion 22a of the imaging table 22 on a front side of the biopsy apparatus 10. Radiation is accordingly irradiated from the radiation source 24 to the breast N in a direction from an axial center of the trunk of the subject W toward the outside, and the MLO imaging is performed.

The CC imaging and the MLO imaging enable not only plain radiography for capturing one radiographic image, but also stereotactic imaging or tomosynthesis imaging while the engagement state between the rotation shaft 18 and the holder section 28 is set to the first state.

Figure 5:
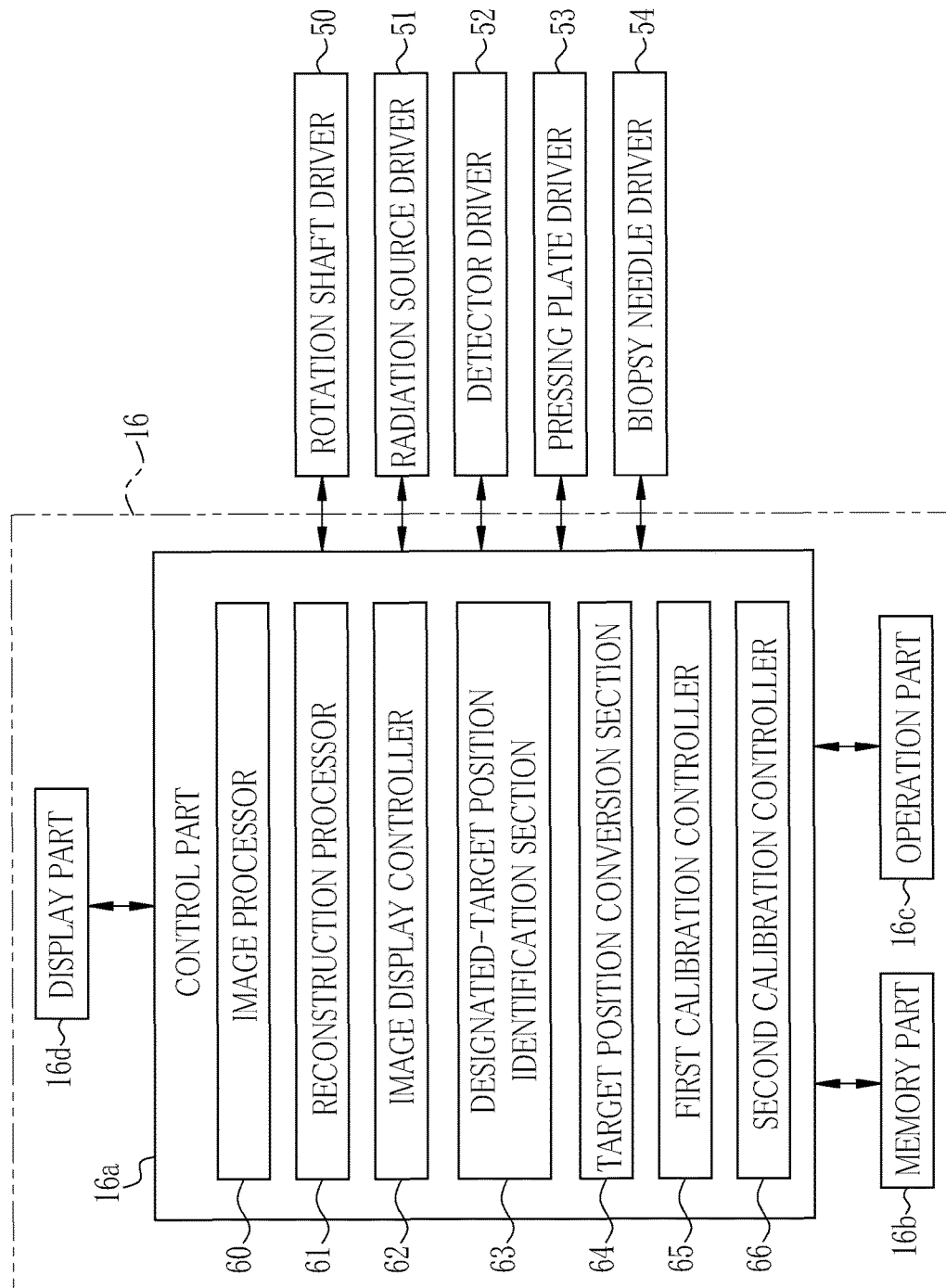
FIG. 5 is a block diagram of an electrical configuration of the biopsy apparatus.

As shown in FIG. 5, the biopsy apparatus 10 includes a rotation shaft driver 50, a radiation source driver 51, a detector driver 52, a pressing plate driver 53, and a biopsy needle driver 54, which are electrically connected to a control part 16a of the PC 16. The rotation shaft driver 50 is provided to the base 14. The support section 29 is rotated by driving the rotation shaft 18 while the engagement state between the rotation shaft 18 and the holder section 28 is set to the first state or the second state. The control part 16a controls the rotation shaft driver 50 so as to set the position of the tube 24a of the radiation source 24.

The radiation source driver 51 is provided to the support section 29, and drives the tube 24a by applying voltage and current to the tube 24a of the radiation source 24. The control part 16a controls the radiation source driver 51 so as to control the timing for irradiating radiation from the tube 24a and the intensity of the radiation.

The pressing plate driver 53 is provided to the holder section 28, and drives the pressing plate 26. The control part 16a controls the pressing driver 53, so as to slide the pressing plate 26 in the Z direction, such that the breast N is compressed against the imaging surface 20 of the imaging table 22 at a predetermined pressing pressure.

The biopsy needle driver 54 is provided to the post section 36 so as to drive the arm section 37 for holding the biopsy needle 40. The control part 16a controls the biopsy needle driver 54, so as to move the arm section 37, such that the position of the tip portion 40a of the biopsy needle 40 is changed. The position of the tip portion 40a of the biopsy needle 40 changed by the biopsy needle driver 54 is represented by the biopsy coordinate system described above.

The control part 16a includes an image processor 60, a reconstruction processor 61, an image display controller 62, a designated-target position identification section 63, a target position conversion section 64, a first calibration controller 65, and a second calibration controller 66. The control part 16a consists of hardware, for example, and operates based on various kinds of computer programs stored in the memory part 16b, so as to realize the function of each of the image processor 60, the reconstruction processor 61, the image display controller 62, and the designated-target position identification section 63, as described later. Incidentally, the configuration of the control part 16a is not limited to this embodiment. For example, the control part 16 may be integrated with a memory part 16b.

The image processor 60 acquires the radiographic image from the radiation detector 42, and subjects the acquired radiographic image to various kinds of image processing such as defect pixel correction and gain correction.

Figure 6:
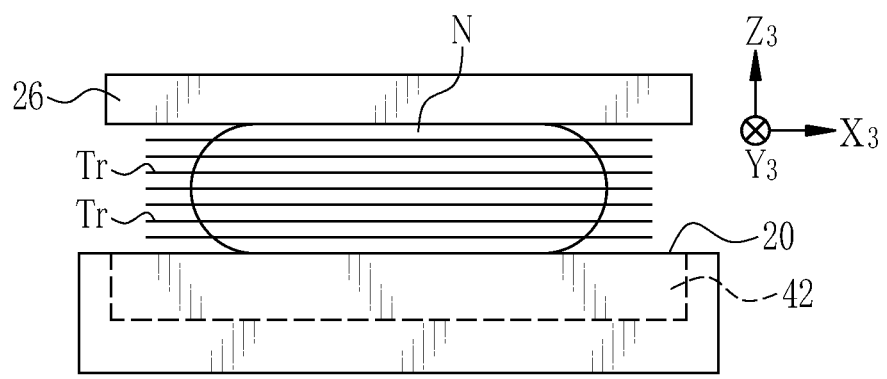
FIG. 6 is a view illustrating a plurality of tomographic images.

The reconstruction processor 61 acquires N number of radiographic images obtained by the tomosynthesis imaging from the radiation detector 42 via the image processor 60 at the time of the tomosynthesis imaging. Then, the reconstruction processor 61 performs reconstruction processing with use of position information of the tomosynthesis tube position $P_{T1}$ to $P_{TN}$ and the N number of radiographic images based on a shift-and-add method or a filtered back projection method. In the reconstruction processing, a plurality of tomographic images Tr parallel to the imaging surface 20 are generated, as shown in FIG. 6. The tomosynthesis image consisting of the plurality of tomographic images Tr is represented by the tomosynthesis coordinate system. Namely, the tomographic images Tr are parallel to a plane along the X-coordinate $X_3$ and Y-coordinate $Y_3$ (hereinafter referred to as $X_3$-$Y_3$ plane), and arranged at regular intervals in the $Z_3$ direction. The tomosynthesis image is stored in the memory part 16b.

Figure 7:
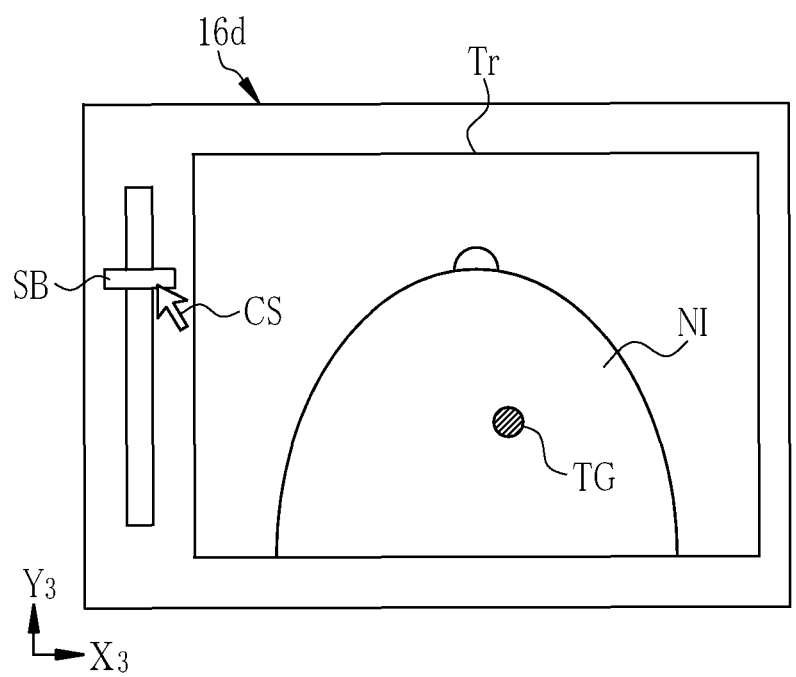
FIG. 7 is a view illustrating a display mode of a tomosynthesis image on a display part.

The image display controller 62 displays the radiographic image generated by the plain radiography, the stereotactic image, or the tomosynthesis image on the display part 16d. In the case where the tomosynthesis image is displayed, the image display controller 62 displays one of the tomographic images Tr of the tomosynthesis image and a slider bar SB on the display part 16d, as shown in FIG. 7. The position of the slider bar SB represents the coordinates of the tomographic image Tr in the $Z_3$ direction (i.e., so-called slice height). The user operates the mouse or the like of the operation part 16c so as to drag the slider bar SB with use of a cursor CS such that the slider bar SB moves upward or downward. Thereby, the user can switch the tomographic images Tr to be displayed on the display part 16d.

Further, the user can designate a lesion position in a breast image NI displayed in the tomographic image Tr as a target TG to be subjected to the biopsy by operating the operation part 16c. The target TG is designated by operating the mouse of the operation part 16c so as to place the cursor CS over the lesion position and clicking a button of the mouse, for example. More specifically, the user observes the breast image NI while switching the tomographic images Tr to be displayed on the display part 16d by operating the slider bar SB, and designates the lesion position such as calcification in the breast image NI as the target TG by operating the mouse.

The designated-target position identification section 63 identifies a three-dimensional position of the target TG designated in the tomographic image Tr of the tomosynthesis image. Specifically, the designated-target position identification section 63 calculates the $Z_3$-coordinate of the tomographic image Tr in which the target TG is designated, and further calculates the $X_3$-coordinate and $Y_3$-coordinate of the target TG in the tomographic image Tr, so as to identify a designated position TP1 of the target TG in the tomosynthesis coordinate system. Hereinafter, the designated position TP1 is referred to as first designated position TP1.

Figure 8:
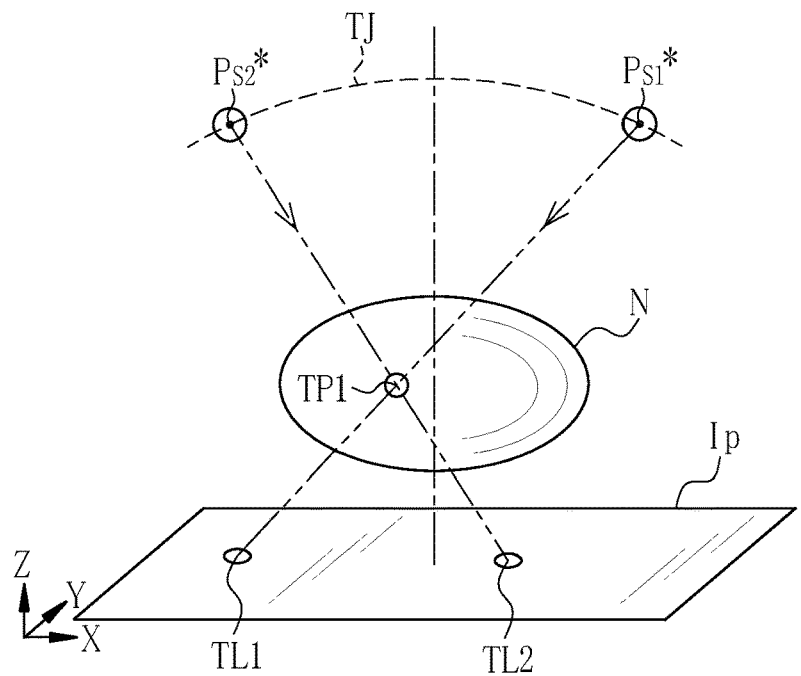
FIG. 8 is a first view explaining target position conversion processing.
Figure 9:
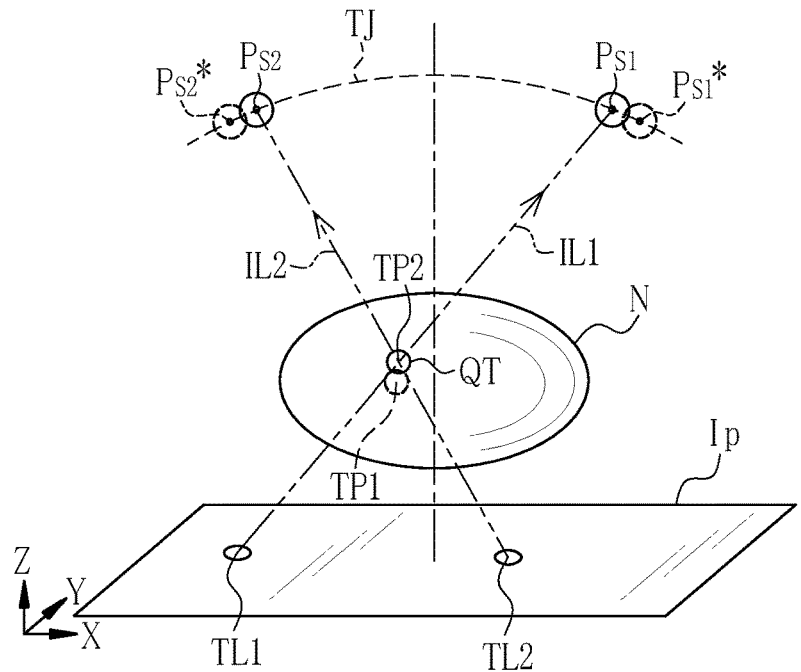
FIG. 9 is a second view explaining the target position conversion processing.

The target position conversion section 64 converts the first designated position TP1 of the target TG identified by the designated-target position identification section 63 into a second designated position TP2 corresponding to the first designated position TP1 in the stereotactic coordinate system. More specifically, the target position conversion section 64 virtually projects the first designated position TP1 toward the radiation detector 42 (see FIG. 2) from calibrated-stereotactic tube positions $P_{S1*}$ and $P_{S2*}$, which have been calibrated in the first calibration processing performed by the first calibration controller 65 to be described later, as shown in FIG. 8. Then, the target position conversion section 64 calculates a first projection position TL1 and a second projection position TL2 in a virtual projection image Ip. The first projection position TL1 and the second projection position TL2 are represented by X-Y coordinates in the radiation detector 42 (i.e., X-Y coordinates in the radiographic image).

Thereafter, the target position conversion section 64 obtains an intersection between a first virtual straight line IL1 and a second virtual straight line IL2, in which the first virtual straight line IL1 connects the first stereotactic tube position $P_{S1}$ and the first projection position TL1, and the second virtual straight line IL2 connects the second stereotactic tube position $P_{S2}$ and the second projection position TL2. The intersection is the second designated position TP2. Incidentally, in the case where the first virtual straight line IL1 and the second virtual straight line IL2 do not intersect with each other, a proximate point at which the first virtual straight line IL1 and the second virtual straight line IL2 are closest to each other is obtained as the intersection. The proximate point is, for example, an intermediate point between a point on the first virtual straight line IL1 which is proximate to the second virtual straight line IL2 and a point on the second virtual straight line IL2 which is proximate to the first virtual straight line IL1.

As described above, the target position conversion section 64 converts the first designated position TP1 designated in the tomosynthesis coordinate system into the second designated position TP2 in the stereotactic coordinate system. The stereotactic coordinate system has been already calibrated relative to the biopsy coordinate system in the calibration processing performed by the second calibration controller 66 as described later. Therefore, the tip portion 40a of the biopsy needle 40 can be adjusted to the target TG with a high degree of accuracy by controlling the biopsy needle driver 54 based on the second designated position TP2 and driving the biopsy needle 40.

Figure 10:
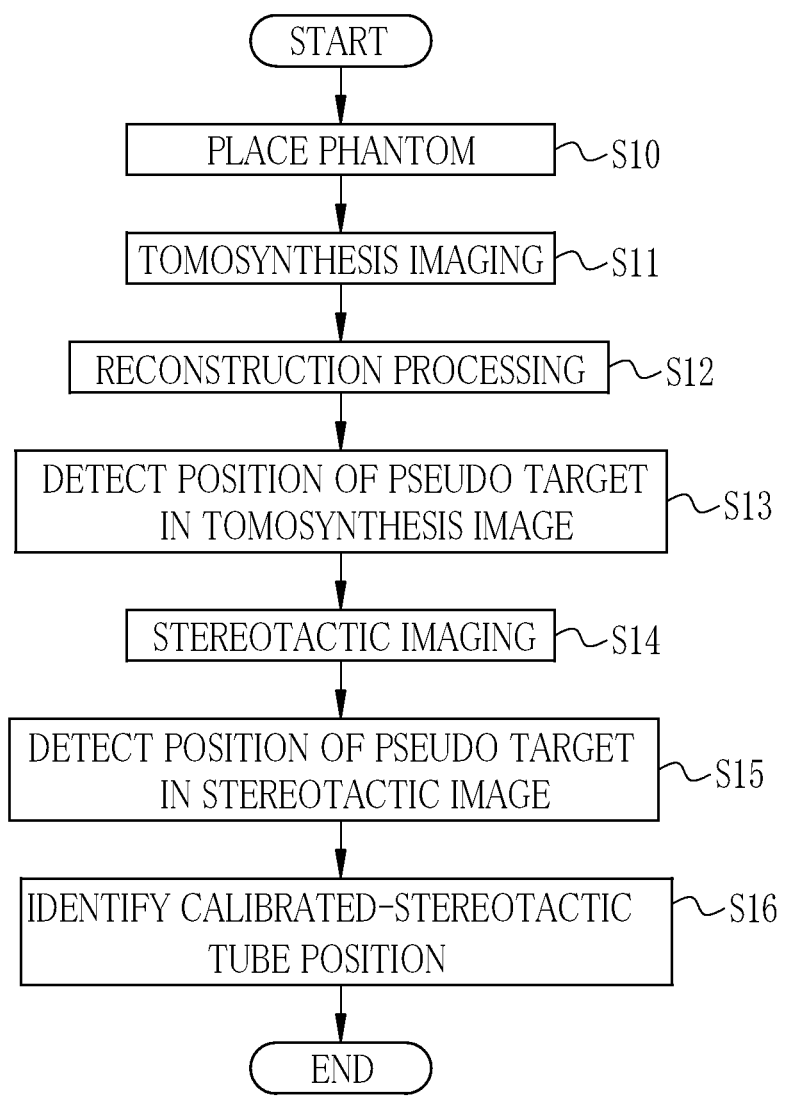
FIG. 10 is a flowchart explaining a procedure of first calibration control.
Figure 11:
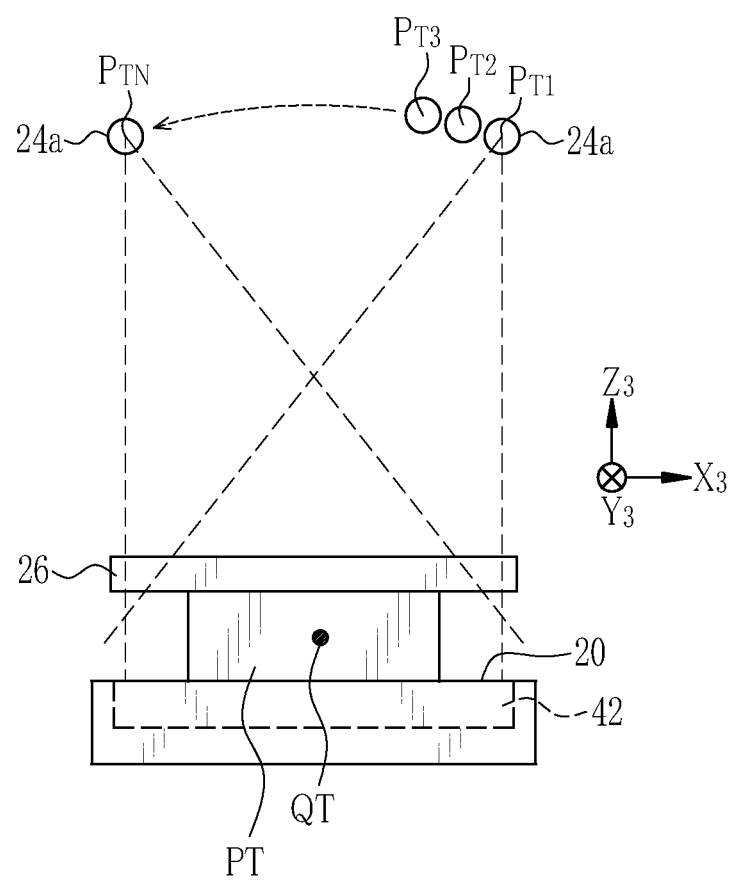
FIG. 11 is a view illustrating a phantom for use in first calibration processing.

The first calibration controller 65 controls the calibration between the stereotactic coordinate system and the tomosynthesis coordinate system in accordance with the procedure shown in FIG. 10. At first, as shown in FIG. 11, a phantom PT is placed on the imaging surface 20 of the imaging table 22 by a user (step S10). In this state, when the user gives an instruction to execute the first calibration processing by operating the operation part 16c, the first calibration controller 65 drives the rotation shaft driver 50, the radiation source driver 51, and the detector driver 52, such that the tomosynthesis imaging described above is performed on the phantom PT as an object to be imaged (step S11). Upon completion of the tomosynthesis imaging, the first calibration controller 65 causes the reconstruction processor 61 to perform reconstruction processing based on the N number of radiographic images obtained by the tomosynthesis imaging, so as to generate a tomosynthesis image consisting of a plurality of tomographic images Tr (step S12).

The phantom PT is obtained by embedding a spherical pseudo target QT in a rectangular parallelepiped material having radiotransparency. The pseudo target QT is made of a radiation absorbent such as lead, and has a size equivalent to that of the tip portion 40a of the biopsy needle 40.

Figure 12:
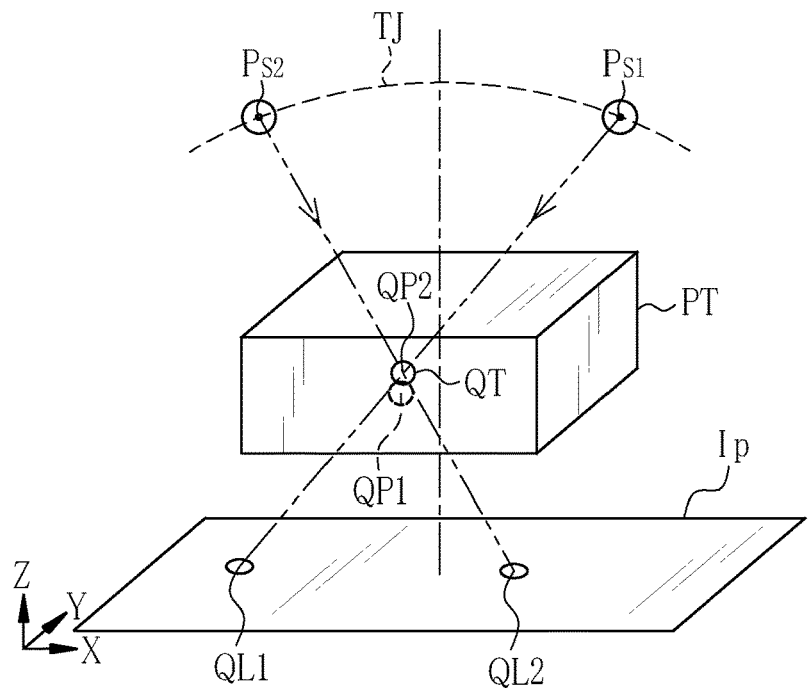
FIG. 12 is a first view explaining the first calibration processing.

The first calibration controller 65 perceives an image of the pseudo target QT existing in the tomosynthesis image with use of pattern matching or the like, so as to detect a position QP1 of the pseudo target QT in the tomosynthesis coordinate system, as shown in FIG. 12 (step S13). Incidentally, the detection of the position QP1 of the pseudo target QT may be performed by the user based on the tomosynthesis image displayed on the display part 16d, as shown in FIG. 7. In this case, the first calibration controller 65 detects the position of the pseudo target QT in the tomographic image Tr designated by the user with use of the cursor CS or the like.

Next, the first calibration controller 65 drives the rotation shaft driver 50, the radiation source driver 51, and the detector driver 52, such that the stereotactic imaging described above is performed on the phantom PT as an object to be imaged (step S14). Upon completion of the stereotactic imaging, the first calibration controller 65 detects a first projection position QL1 and a second projection position QL2 of the pseudo target QT projected on each of the radiographic images (i.e., projection images) Ip constituting the stereotactic image (step S15). As shown in FIG. 12, the first projection position QL1 is a projection position of the pseudo target QT with use of radiation irradiated from the tube 24a set at the stereotactic tube position $P_{S1}$, and the second projection position QL2 is a projection position of the pseudo target QT with use of radiation irradiated from the tube 24a set at the stereotactic tube position $P_{S2}$. The first and second projection positions QL1 and QL2 are represented by the X-Y coordinates in the radiation detector 42 (i.e., X-Y coordinates in the radiographic image Ip). In FIG. 12, the symbol "QP2" represents the position of the pseudo target QT in the stereotactic coordinate system.

Specifically, the first calibration controller 65 perceives an image of the pseudo target QT existing in the projection image Ip with use of pattern matching or the like so as to detect the first projection position QL1 and the second projection position QL2. Incidentally, the detection of the first projection position QL1 and the second projection position QL2 may be performed by displaying the stereotactic image on the display part 16d by the user. In this case, the first calibration controller 65 detects the position of the pseudo target QT in the projection image Ip designated by the user with use of the cursor CS or the like.

Figure 13:
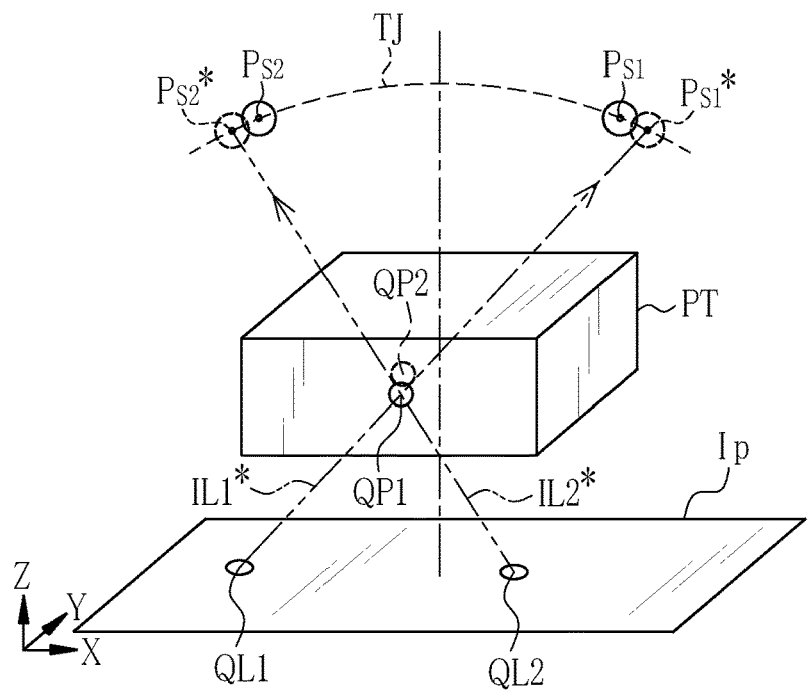
FIG. 13 is a second view explaining the first calibration processing.

As shown in FIG. 13, the first calibration controller 65 identifies the position of the tube 24a in a direction connecting the first projection position QL1 and the position QP1 of the pseudo target QT identified in the tomosynthesis imaging as the calibrated-stereotactic tube position $P_{S1*}$, and identifies the position of the tube 24a in a direction connecting the second projection position QL2 and the position QP1 of the pseudo target QT identified in the tomosynthesis imaging as the calibrated-stereotactic tube position $P_{S2*}$ (step S16).

Specifically, a virtual straight line IL1* connecting the first projection position QL1 and the position QP1 of the pseudo target QT is extended toward the tube 24a, and an intersection between an arc-like trajectory TJ of the tube 24a and the extended virtual straight line IL1* (or a proximate point on the trajectory TJ, which is proximate to the extended virtual straight line IL1*, in the case where the trajectory TJ and the extended virtual straight line IL1* do not intersect with each other) is identified as a first calibrated-stereotactic tube position $P_{S1*}$. In the similar manner, a virtual straight line IL2* connecting the second projection position QL2 and the position QP1 of the pseudo target QT is extended toward the tube 24a, and an intersection between the arc-like trajectory TJ of the tube 24a and the extended virtual straight line IL2* (or a proximate point on the trajectory TJ, which is proximate to the extended virtual straight line IL2*, in the case where the trajectory TJ and the extended virtual straight line IL2* do not intersect with each other) is identified as a second calibrated-stereotactic tube positions $P_{S2*}$. The first calibrated-stereotactic tube positions $P_{S1*}$ corresponds to the first stereotactic tube position $P_{S1}$ in the stereotactic coordinate system, and the second calibrated-stereotactic tube positions $P_{S2*}$ corresponds to the second stereotactic tube position $P_{S2}$ in the stereotactic coordinate system.

Thereafter, when the first calibration controller 65 inputs the identified first and second calibrated-stereotactic tube positions $P_{S1*}$ and $P_{S2*}$ to the target position conversion section 64, the first calibration processing is completed. It is obvious from the first calibration processing described above that the projection positions of the target TG to be projected actually in the stereotactic imaging (corresponding to the first and second projection positions TL1 and TL2) are obtained by virtually projecting the first designated position TP1 designated in the tomosynthesis image toward the radiation detector 42 from the first and second calibrated-stereotactic tube positions $P_{S1*}$ and $P_{S2*}$. The target position conversion section 64 obtains the second designated position TP2 in the stereotactic coordinate system based on the projection positions and the first and second stereotactic tube positions $P_{S1}$ and $P_{S2}$ at the time of the stereotactic imaging.

The second calibration controller 66 performs calibration control between the biopsy coordinate system and the stereotactic coordinate system in accordance with a method disclosed in Japanese Patent Laid-Open Publication No. 2010-75316 or the like. The second calibration processing is performed by attaching a calibration biopsy needle (not shown in the drawing) having a tip portion formed into a spherical shape, instead of the biopsy needle 40, to the arm section 37, and performing the stereotactic imaging. The second calibration processing is executed in the case where the user gives an instruction to execute the second calibration processing by operating the operation part 16c.

More specifically, the second calibration controller 66 controls the rotation shaft driver 50, the radiation source driver 51, the detector driver 52, and the biopsy needle driver 54, so as to calculate a deviation amount between the biopsy coordinate system and the stereotactic coordinate system based on position information of the tip portion of the calibration biopsy needle in the stereotactic image obtained by the stereotactic imaging and position information of the tip portion of the calibration biopsy needle positioned by the biopsy needle driver 54. Further, the second calibration controller 66 creates calibration data for associating the biopsy coordinate system with the stereotactic coordinate system. The calibration data is stored in the memory part 16b.

During the biopsy operation, the biopsy needle driver 54 corrects the deviation amount between the biopsy coordinate system and the stereotactic coordinate system based on the calibration data stored in the memory part 16b, and then drives the biopsy needle 40.

Note that, the second calibration processing may be performed with use of a phantom provided with a plurality of markers, as disclosed in U.S. Pat. No. 5,964,715 (corresponding to Japanese Patent Laid-Open Publication No. 10-201749). In this case, in a state that the biopsy needle 40 is inserted into the phantom and the tip portion 40a of the biopsy needle 40 is manually adjusted to a position of each of the markers, position information of each of the markers represented by the biopsy coordinate system is acquired. Next, an image of the phantom is captured by the stereotactic imaging, so as to obtain the position information of each of the markers represented by the stereotactic coordinate system. In the case where deviation occurs between the position information of the marker represented by the biopsy coordinate system and the position information of the marker represented by the stereotactic coordinate system as a result of comparison therebetween, the biopsy coordinate system is calibrated so as to cancel the deviation.

In the second calibration processing, bothersome tasks such as attachment of the calibration biopsy needle to the arm section 37 and insertion of the biopsy needle 40 into the phantom provided with the markers are required for a user, and therefore the second calibration processing is not easy. In contrast, in the first calibration processing, since it is sufficient to place the phantom PT and give an instruction to execute the image capturing (i.e., tomosynthesis imaging and stereotactic imaging), it is easy for a user to perform the first calibration processing.

In this embodiment, the control part 16a, the rotation shaft driver 50, the radiation source driver 51, the detector driver 52, the radiation source 24, and the radiation detector 42 constitute a stereotactic image generator described in the scope of claims. Further, the control part 16a, the rotation shaft driver 50, the radiation source driver 51, the detector driver 52, radiation source 24, the radiation detector 42, and the reconstruction processor 61 constitute a tomosynthesis image generator described in the scope of claims.

Figure 14:
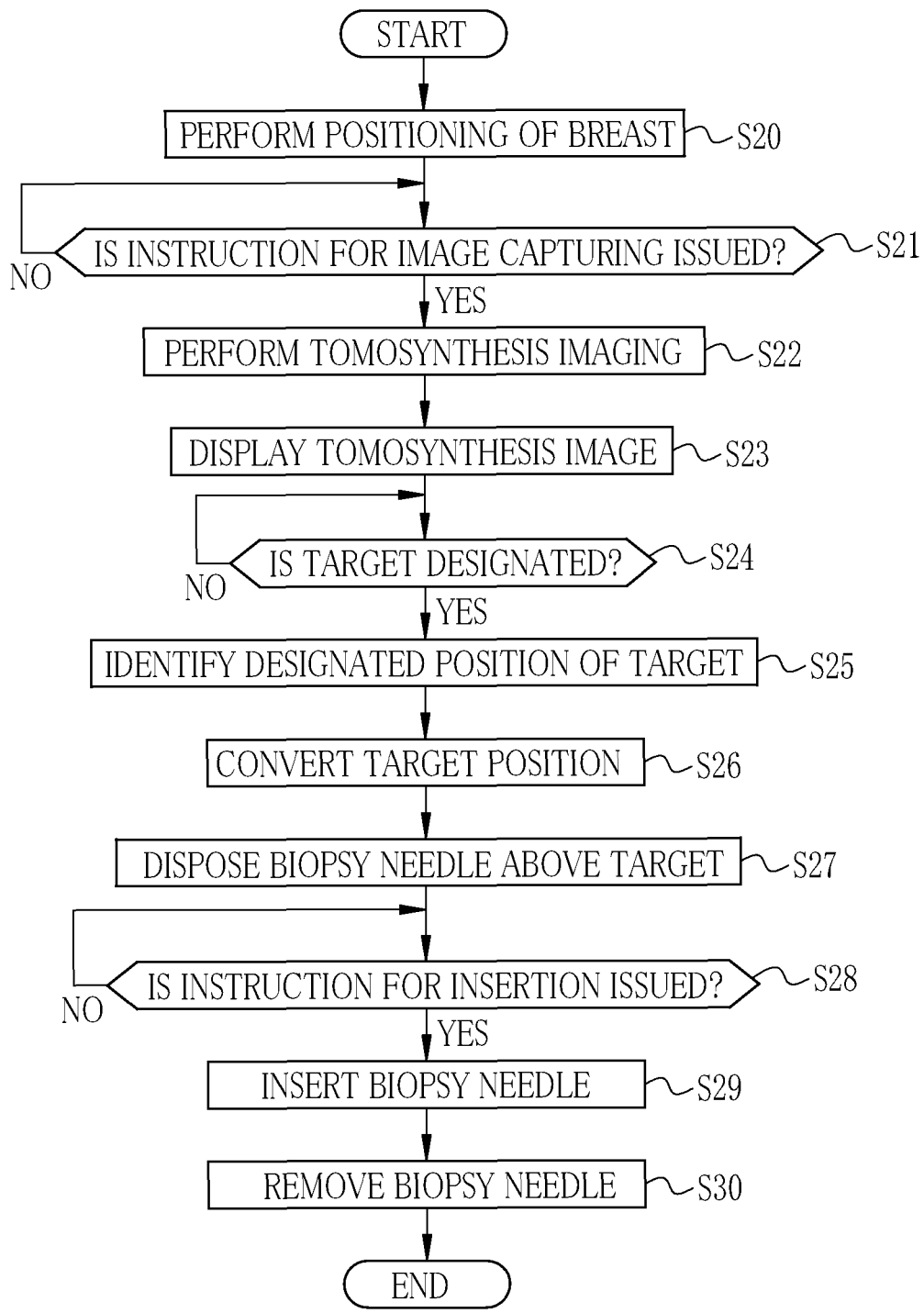
FIG. 14 is a flowchart explaining an operation of the biopsy apparatus.

Next, an operation of the biopsy apparatus 10 constituted as described above is explained hereinbelow by referring to a flowchart shown in FIG. 14. At first, a user such as a doctor performs positioning of the breast N of the subject W relative to the imaging table 22 (step S20). Specifically, after the breast N is put on a predetermined position of the imaging surface 20 of the imaging table 22, the pressing plate 26 is moved toward the imaging surface 20 to compress the breast N. Thereby, the positioning of the breast N is performed.

After completion of the positioning of the breast N, when an instruction to perform image capturing is issued from the user with use of the operation part 16c (YES in step S21), the tomosynthesis imaging is performed (step S22). After completion of the tomosynthesis imaging, the reconstruction processor 61 performs the reconstruction processing to generate a tomosynthesis image, and the tomosynthesis image is displayed on the display part 16d (step S23).

The user observes each of the tomographic images Tr of the tomosynthesis image displayed on the display part 16d. In the case where the user finds a lesion such as calcification, the user operates the mouse or the like of the operation part 16c to adjust the cursor CS to the lesion position, and clicks the button of the mouse. Thereby, the lesion position is designated as the target TG. When the target TG is designated as described above (YES in step S24), the designated-target position identification section 63 identifies the first designated position TP1 of the target TG in the tomosynthesis coordinate system (step S25, i.e., target position identifying step).

After the first designated position TP1 is identified, the target position conversion section 64 converts the first designated position TP1 into the second designated position TP2 in the stereotactic coordinate system by the processing described above (step S26, i.e., target position converting step). In the conversion processing, the position information of the first and second calibrated-stereotactic tube positions $P_{S1*}$ and $P_{S2*}$ which have been obtained in the first calibration processing is used.

After the second designated position TP2 is determined, the biopsy needle 40 is disposed above the second designated position TP2 (step S27). Concurrently, the biopsy needle driver 54 corrects the deviation amount between the biopsy coordinate system and the stereotactic coordinate system based on the calibration data stored in the memory part 16b, and then drives the biopsy needle 40. Accordingly, the tip portion 40a of the biopsy needle 40 is disposed above the second designated position TP2 in the stereotactic coordinate system (namely, disposed at a position of which $X_2$-coordinate and $Y_2$-coordinate are the same as those of the second designated position TP2 and of which $Z_2$-coordinate is different from that of the second designated position TP2).

Thereafter, upon issuance of an instruction to insert the biopsy needle 40 from the user with use of the operation part 16c (YES in step S28), the biopsy needle 40 is moved downward in the $Z_2$ direction and inserted into the breast N, and then the tip portion 40a of the biopsy needle 40 reaches the second designated position TP2 (step S29, i.e., inserting step). In this state, a piece of tissue is extracted from the breast N through the tip portion 40a. Then, the biopsy needle 40 is removed from the breast N (step S30), and the biopsy is completed.

As described above, the tomosynthesis coordinate system is associated with the stereotactic coordinate system by the first calibration processing, and the stereotactic coordinate system is associated with the biopsy coordinate system by the second calibration processing. Therefore, it is possible to insert the biopsy needle 40 into the garget TG with a high degree of accuracy based on the first designated position TP1 of the target TG designated in the tomosynthesis coordinate system.

According to the tomosynthesis imaging, the tube 24a of the radiation source 24 is set at a plurality of positions so as to perform image capturing. An error in setting each of the positions of the tube 24a results in deviation in the tomosynthesis coordinate system, and therefore, the deviation amount of the tomosynthesis coordinate system from the biopsy coordinate system is considered to be larger than that of the stereotactic coordinate system from the biopsy coordinate system. In view of the above, in the case where the position of the target TG is designated based on the tomosynthesis image as with this embodiment, it is necessary to perform the calibration between the coordinate systems with a higher degree of accuracy in comparison with the case where the position of the target TG is designated based on the stereotactic image.

To perform the calibration between the tomosynthesis coordinate system and the biopsy coordinate system with a high degree of accuracy in a conventional manner is troublesome and a burden on the user. However, according to this embodiment, the tomosynthesis coordinate system is associated with the biopsy coordinate system through the stereotactic coordinate system, and it is sufficient to place the phantom PT and perform the image capturing (i.e., the tomosynthesis imaging and the stereotactic imaging) so as to perform the calibration processing between the tomosynthesis coordinate system and the stereotactic coordinate system. Accordingly, it is possible to readily perform the calibration processing between the tomosynthesis coordinate system and the stereotactic coordinate system according to this embodiment.

Second Embodiment

According to the above embodiment, the control part 16a controls the rotation shaft driver 50 so as to set the position of the tube 24a of the radiation source 24 (i.e., the stereotactic tube positions $P_{S1}$ and $P_{S2}$ and the tomosynthesis tube positions $P_{T1}$ to $P_{TN}$) and each of the reconstruction processor 61 and the target position conversion section 64 performs the processing based on the position information of the tube 24a set by the control part 16a. However, the processing may be performed based on a value obtained by correcting the position information of the tube 24a with use of setting error information of the tube 24a.

Figure 15:
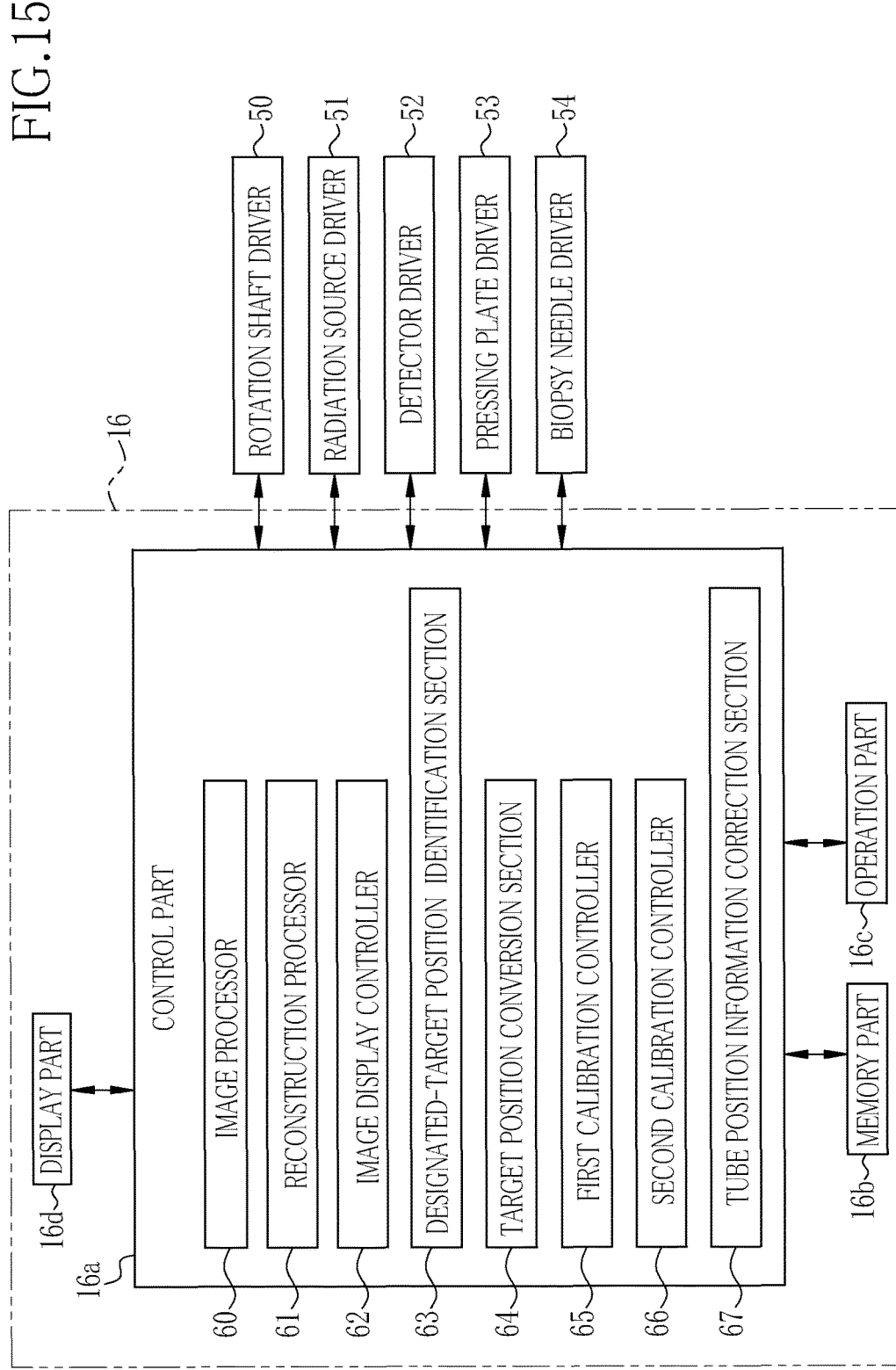
FIG. 15 is a view illustrating a configuration of a control part according to a second embodiment.

According to a second embodiment, as shown in FIG. 15, the control part 16a includes a tube position information correction section 67. The tube position information correction section 67 holds the setting error information of the tube 24a, and corrects the set position of the tube 24a (i.e., the stereotactic tube position $P_{S1}$ and $P_{S2}$ and the tomosynthesis tube positions $P_{T1}$ to $P_{TN}$). The setting error information is acquired based on a plurality of radiographic images (i.e., the projection images) which have been obtained by disposing markers or the like in an imaging area, as disclosed in Japanese Patent Laid-Open Publication No. 2013-015651. The setting error information is a difference between the set position of the tube 24a set by the control part 16a (i.e., designed value) and the position of the tube 24a actually disposed by the rotation shaft driver 50 (i.e., true value). A configuration of the second embodiment other than the above features is the same as that of the first embodiment.

According to the second embodiment, the reconstruction processor 61 performs the reconstruction processing based on the tomosynthesis tube positions $P_{T1}$ to $P_{TN}$ corrected by the tube position information correction section 67.

Further, the target position conversion section 64 creates the first virtual straight line IL1 connecting the first projection position TL1 to the first stereotactic tube position $P_{S1}$ which has been corrected by the tube position information correction section 67, and the second virtual straight line IL2 connecting the second projection position TL2 to the second stereotactic tube position $P_{S2}$ which has been corrected by the tube position information correction section 67. Thereafter, the target position conversion section 64 obtains an intersection between the first virtual straight line IL1 and the second virtual straight line IL2. Incidentally, in the case where the first virtual straight line IL1 and the second virtual straight line IL2 do not intersect with each other as with the above embodiment, a proximate point at which the first virtual straight line IL1 and the second virtual straight line IL2 are closest to each other is obtained as the intersection.

Even in the case where the tube position information correction section 67 corrects the tube position information as described above, the tube position information after the correction is slightly deviated from the true value. In particular, the deviation of each of the tomosynthesis tube positions $P_{T1}$ to $P_{TN}$ after the correction from the true value tends to affect the reconstruction processing, and causes the deviation of the tomosynthesis coordinate system from the biopsy coordinate system and the stereotactic coordinate system. Therefore, also in the case where the tube position information is corrected based on the setting error information, the present invention is effective.

Further, according to the first and second embodiments, the mammography apparatus for capturing an image of the breast N as the subject to be examined, to which the biopsy function is added, is used as the biopsy apparatus 10. However, the subject to be examined is not limited to the breast, and the biopsy apparatus 10 may be obtained by adding the biopsy function to a radiography apparatus in which a subject to be examined is another site. Furthermore, the radiation to be used for the radiography is not limited to X-rays, and may be γ-rays or the like.

Moreover, recently, a tomosynthesis imaging function is added by so-called retrofit in which the control function and the image processing function of an existing stereotactic biopsy apparatus are modified. The present invention is suitable for the stereotactic biopsy apparatus to which the tomosynthesis imaging function is added by the retrofit.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. A biopsy apparatus comprising:
   a radiation source for irradiating radiation toward a subject to be examined from a tube;
   a radiation detector for detecting radiation which has been irradiated from the radiation source and passed through the subject so as to generate a radiographic image;
   a stereotactic image generator for generating a stereotactic image, which consists of two radiographic images generated by the radiation detector and is represented by a stereotactic coordinate system, by irradiating radiation from the tube disposed at two stereotactic tube positions each having a different angle relative to the subject;
   a tomosynthesis image generator for generating a tomosynthesis image, which is represented by a tomosynthesis coordinate system, by irradiating radiation from the tube disposed at a plurality of tomosynthesis tube positions each having a different angle relative to the subject and performing reconstruction of a plurality of tomographic images from a plurality of radiographic images generated by the radiation detector;
   a biopsy needle driver for driving a biopsy needle based on a biopsy coordinate system calibrated with respect to the stereotactic coordinate system so as to insert the biopsy needle into the subject; and
   a processor configured to:
   identify a position of a target designated based on the tomosynthesis image as a first designated position; and
   obtain two projection positions by virtually projecting the first designated position to the image detector from two calibrated-stereotactic tube positions which have been calibrated into the tomosynthesis coordinate system, and converting the first designated position into a second designated position in the stereotactic coordinate system based on the stereotactic tube positions and the projection positions.

2. The biopsy apparatus according to claim 1, further comprising a tube position information correction section for correcting the stereotactic tube positions and the tomosynthesis tube positions based on setting error information of the tube, wherein
   the tomosynthesis image generator performs the reconstruction based on the tomosynthesis tube positions corrected by the tube position information correction section, and
   the processor obtains the second designated position based on the stereotactic tube positions corrected by the tube position information correction section.

3. The biopsy apparatus according to claim 1, further comprising:
   a display part on which the tomosynthesis image is displayed;
   wherein the processor receives a designated position of the target based on the tomosynthesis image displayed on the display part, wherein
   the processor identifies a position in the tomosynthesis coordinate system, which is designated by the operation part, as the first designated position.

4. The biopsy apparatus according to claim 1, further comprising a calibration controller for making the tomosynthesis image generator generate a tomosynthesis image in a state that an object to be imaged is a phantom having a pseudo target so as to detect a position of the pseudo target in the tomosynthesis coordinate system, and making the stereotactic image generator generate a stereotactic image so as to detect a position on the radiation detector toward which the pseudo target is projected, and identifying a position of the tube in a direction connecting the position toward which the pseudo target is projected and the position of the pseudo target in the tomosynthesis coordinate system as the calibrated-stereotactic tube position.

5. The biopsy apparatus according to claim 1, further comprising a memory part in which calibration data for associating the biopsy coordinate system with the stereotactic coordinate system is stored, wherein the biopsy needle driver corrects a deviation amount between the biopsy coordinate system and the stereotactic coordinate system based on the calibration data, and then drives the biopsy needle.

6. An operation method of a biopsy apparatus, the biopsy apparatus including: a radiation source for irradiating radiation toward a subject to be examined from a tube; a radiation detector for detecting radiation which has been irradiated from the radiation source and passed through the subject so as to generate a radiographic image; a stereotactic image generator for generating a stereotactic image, which consists of two radiographic images generated by the radiation detector and is represented by a stereotactic coordinate system, by irradiating radiation from the tube disposed at two stereotactic tube positions each having a different angle relative to the subject; a tomosynthesis image generator for generating a tomosynthesis image, which is represented by a tomosynthesis coordinate system, by irradiating radiation from the tube disposed at a plurality of tomosynthesis tube positions each having a different angle relative to the subject and performing reconstruction of a plurality of tomographic images from a plurality of radiographic images generated by the radiation detector; and a biopsy needle driver for driving a biopsy needle based on a biopsy coordinate system calibrated with respect to the stereotactic coordinate system so as to insert the biopsy needle into the subject, the operation method comprising the steps of:

identifying a position of a target designated based on the tomosynthesis image as a first designated position;

obtaining two projection positions by virtually projecting the first designated position to the image detector from two calibrated-stereotactic tube positions which have been calibrated into the tomosynthesis coordinate system, and converting the first designated position into a second designated position in the stereotactic coordinate system based on the stereotactic tube positions and the projection positions;

obtaining an intersection between a first virtual straight line and a second virtual straight line as the second designated position, the first virtual straight line connecting a first projection position and a first stereotactic tube position, the second virtual straight line connecting a second projection position and a second stereotactic tube position, the first projection position being obtained by virtually projecting the first designated position from a first calibrated-stereotactic tube position of the two calibrated-stereotactic tube positions toward the image detector, the first stereotactic tube position of the two stereotactic tube positions corresponding to the first calibrated-stereotactic tube position, the second projection position being obtained by virtually projecting the first designated position from a second calibrated-stereotactic tube position of the two calibrated-stereotactic tube positions toward the image detector, and the second stereotactic tube position of the two stereotactic tube positions corresponding to the second calibrated-stereotactic tube position; and inserting the biopsy needle into the subject based on the second designated position.

\* \* \* \* \*